US012116368B2

(12) United States Patent
Samas et al.

(10) Patent No.: US 12,116,368 B2
(45) Date of Patent: Oct. 15, 2024

(54) PYRROLO[2,3-D]PYRIMIDINE TOSYLATE SALT, CRYSTALLINE FORM THEREOF AND MANUFACTURING PROCESS AND INTERMEDIATES THERETO

(71) Applicant: Pfizer Inc., New York, NY (US)

(72) Inventors: Brian Matthew Samas, Branford, CT (US); Yong Tao, Salem, CT (US); Douglas James Critcher, Sandwich (GB); David Sydney Bernard Daniels, Sandwich (GB); Kevin Paul Girard, Quaker Hill, CT (US); Gregory Scott Goeken, Mystic, CT (US); Peter Robert Rose, Ledyard, CT (US)

(73) Assignee: Pfizer Inc., New York, NY (US)

( * ) Notice: Subject to any disclaimer, the term of this patent is extended or adjusted under 35 U.S.C. 154(b) by 727 days.

(21) Appl. No.: 17/286,018

(22) PCT Filed: Oct. 21, 2019

(86) PCT No.: PCT/IB2019/058940
§ 371 (c)(1),
(2) Date: Apr. 16, 2021

(87) PCT Pub. No.: WO2020/084435
PCT Pub. Date: Apr. 30, 2020

(65) Prior Publication Data
US 2021/0387989 A1 Dec. 16, 2021

Related U.S. Application Data

(60) Provisional application No. 62/748,628, filed on Oct. 22, 2018.

(51) Int. Cl.
*C07D 487/04* (2006.01)
(52) U.S. Cl.
CPC ........ *C07D 487/04* (2013.01); *C07B 2200/13* (2013.01)
(58) Field of Classification Search
CPC .................................... C07D 487/04
USPC ........................................ 544/280
See application file for complete search history.

(56) References Cited

FOREIGN PATENT DOCUMENTS

| CN | 105859721 A | 8/2016 |
|----|-------------|--------|
| EP | 3318565 A1 | 5/2018 |
| JP | 2016539137 A | 12/2016 |
| JP | 2018502077 A | 1/2018 |
| TW | 201524977 A | 7/2015 |
| WO | 99/65908 A1 | 12/1999 |
| WO | 2015083028 A1 | 6/2015 |

OTHER PUBLICATIONS

Telliez et al., ACS Chemical Biology (2016), 11(12), 3442-3451.*
Thorarensen et al., Journal of Medicinal Chemistry (2017), 60(5), 1971-1993.*
Casimiro-Garcia et al., Journal of Medicinal Chemistry (2018), 61(23), 10665-10699.*
Bastin et al., "Salt Selection and Optimisation Procedures for Pharmaceutical New Chemical Entities", Organic Process Research & Development, 2000, 427-435, 4.
Caira, Mino R., "Crystalline Polymorphism of Organic Compounds", Topics in Current Chemistry, 1998, 163-208, 198.
Greene et al., "Protection for the Amino Group", Protective Groups in Organic Synthesis, 2019, 494-581.
Morissette et al., "High-throughput crystallization: polymorphs, salts, co-crystals and solvates of pharmaceutical solids", Advanced Drug Delivery Reviews, 2004, 275-300, 56.
PCT International Search Report and Written Opinion for International Application No. PCT/IB2019/058940 mailed on Jan. 16, 2020.
Telliez et al, "Discovery of a JAK3-Selective Inhibitor: Functional Differentiation of JAK3-Selective Inhibition over pan-JAK or JAK1-Selective Inhibition", ACS Chemical Biology 11(12):3442-3451 (2016).
Thorarensen et al, "Design of a Janus Kinase 3 (JAK3) Specific Inhibitor 1-((2S,5R)-5-((7H-Pyrrolo[2,3d] pyrimidin-4-yl)amino)-2-methylpiperidin-1-yl)prop-2-en-1-one (PF-06651600) Allowing for the Interrogation of JAK3 Signaling in Humans", Journal of Medicinal Chemistry 60(5):1971-1993 (2017).

* cited by examiner

*Primary Examiner* — Niloofar Rahmani
(74) *Attorney, Agent, or Firm* — A. David Joran

(57) ABSTRACT

The present invention discloses a novel p-toluenesulfonic acid salt and a crystalline polymorphic Form 1 of said salt of 1-((2S,5R)-5-((7H-pyrrolo[2,3-d]pyrimidin-4-yl)amino)-2-methylpiperidin-1-yl)prop-2-en-1-one, pharmaceutical composition containing the same, as well as preparations and uses thereof. The present invention also discloses a novel phosphoric acid salt of 1-((2S,5R)-5-((7H-pyrrolo[2,3-d]pyrimidin-4-yl)amino)-2-methylpiperidin-1-yl)prop-2-en-1-one, pharma-ceutical composition containing the same, as well as preparations and uses thereof.

6 Claims, 3 Drawing Sheets

PYRROLO[2,3-D]PYRIMIDINE TOSYLATE SALT, CRYSTALLINE FORM THEREOF AND MANUFACTURING PROCESS AND INTERMEDIATES THERETO

FIELD OF THE INVENTION

The present invention relates to a p-toluenesulfonic acid salt of 1-((2S,5R)-5-((7H-pyrrolo[2,3-d]pyrimidin-4-yl)amino)-2-methylpiperidin-1-yl)prop-2-en-1-one. The present invention also relates to a crystalline form thereof and pharmaceutical compositions comprising the p-toluenesulfonic acid salt of 1-((2S,5R)-5-((7H-pyrrolo[2,3-d]pyrimidin-4-yl)amino)-2-methylpiperidin-1-yl)prop-2-en-1-one, and a manufacturing process and intermediates for preparation thereof. The present invention also discloses a novel phosphoric acid salt of 1-((2S,5R)-5-((7H-pyrrolo[2,3-d]pyrimidin-4-yl)amino)-2-methylpiperidin-1-yl)prop-2-en-1-one. The invention further relates to the use of the salts or respective crystalline form in the treatment of various diseases and conditions.

BACKGROUND OF THE INVENTION 1-((2S,5R)-5-((7H-Pyrrolo[2,3-d]pyrimidin-4-yl)amino)-2-methylpiperidin-1-yl)prop-2-en-1-one has the structural formula:

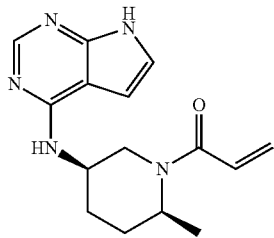 [SMILES: C=CC(=O)N1C[C@H](Nc2ncnc3[nH]ccc23)CC[C@@H]1C]

The synthesis of 1-((2S,5R)-5-((7H-pyrrolo[2,3-d]pyrimidin-4-yl)amino)-2-methylpiperidin-1-yl)prop-2-en-1-one is described in WO2015/083028, commonly assigned to the assignee of the present invention and which is incorporated herein by reference in its entirety. 1-((2S,5R)-5-((7H-Pyrrolo[2,3-d]pyrimidin-4-yl)amino)-2-methylpiperidin-1-yl)prop-2-en-1-one is useful as an inhibitor of protein kinases, such as the enzyme Janus Kinase (JAK) and as such is useful therapy as an immunosuppressive agent for organ transplants, xeno transplantation, lupus, multiple sclerosis, rheumatoid arthritis, psoriasis, Type I diabetes and complications from diabetes, cancer, asthma, atopic dermatitis, autoimmune thyroid disorders, ulcerative colitis, Crohn's disease, alopecia, vitiligo, Alzheimer's disease, leukemia and other indications where immunosuppression would be desirable. See *ACS Chem. Biol.*, 2016, 11 (12), pp 3442-3451. The present invention relates to a novel p-toluenesulfonic acid salt and crystalline solid form of the said salt of 1-((2S,5R)-5-((7H-pyrrolo[2,3-d]pyrimidin-4-yl)amino)-2-methylpiperidin-1-yl)prop-2-en-1-one that demonstrate improved properties for use in a pharmaceutical dosage form, particularly for oral dosage forms.

Based on a chemical structure, it has not been straightforward to predict with any degree of certainty whether a compound will crystallize, under what conditions it will crystallize, how many crystalline solid forms of the compound might exist, or the solid-state structure of any of those forms. A key characteristic of any crystalline drug is the polymorphic behavior of such a material. In general, crystalline forms of drugs are preferred over noncrystalline forms of drugs, in part, because of their superior stability. For example, in many situations, a noncrystalline drug converts to a crystalline drug form upon storage. Because noncrystalline and crystalline forms of a drug typically have differing physical properties and chemical properties, such interconversion may be undesirable for safety reasons in pharmaceutical usage. The different physical properties exhibited by different solid forms of a pharmaceutical compound can affect important pharmaceutical parameters such as storage, compressibility, density (important in formulation and product manufacturing), and dissolution rates (important in determining bioavailability). Stability differences may result from changes in chemical reactivity (e.g., differential hydrolysis or oxidation, such that a dosage form comprising a certain polymorph can discolor more rapidly than a dosage form comprising a different polymorph), mechanical changes (e.g., tablets can crumble on storage as a kinetically favored crystalline form converts to thermodynamically more stable crystalline form), or both (e.g., tablets of one polymorph can be more susceptible to breakdown at high humidity). Solubility differences between polymorphs may, in extreme situations, result in transitions to crystalline forms that lack potency. In addition, the physical properties of a crystalline form may also be important in pharmaceutical processing. For example, a particular crystalline form may form solvates more readily or may be more difficult to filter and wash free of impurities than other crystalline forms (i.e., particle shape and size distribution might be different between one crystalline form relative to other forms).

There is typically no one ideal physical form of a drug because different physical forms provide different advantages. The search for the most stable form is arduous, and the outcome is unpredictable. Thus, it is important to seek a variety of unique drug forms, e.g., salts, polymorphs, noncrystalline forms, which may be used in various formulations. The selection of a drug form for a specific formulation or therapeutic application requires consideration of a variety of properties, and the best form for a particular application may be one which has one specific important good property while other properties may be acceptable or marginally acceptable.

The successful development of a drug requires that it meet certain general requirements to be a therapeutically effective treatment for patients. These requirements fall into three categories: (1) requirements for successful manufacture of dosage forms; (2) requirements for successful drug delivery and disposition after the drug formulation has been administered to the patient; and, (3) requirements for a suitable shelf-life for the dosage form to allow adequate time for manufacture, packaging, storage and use by the patient.

Different crystalline solid forms of the same compound often possess different solid-state properties such as melting point, solubility, dissolution rate, hygroscopicity, powder flow, mechanical properties, chemical stability and physical stability. These solid-state properties may offer advantages in filtration, drying, dosage form manufacturing unit operations and in vivo performance. Thus, once different crystalline solid forms of the same compound have been identified, the optimum crystalline solid form under any given set of processing and manufacturing conditions may be determined as well as the different solid-state properties of each crystalline solid form.

Polymorphs of a molecule can be obtained by a number of methods known in the art. Such methods include, but are not limited to, melt recrystallization, melt cooling, solvent recrystallization, desolvation, rapid evaporation, rapid cooling, slow cooling, vapor diffusion and sublimation. Polymorphs can be detected, identified, classified and characterized using well-known techniques such as, but not limited to, differential scanning calorimetry (DSC), thermogravimetry (TGA), X-ray powder diffractometry (XRPD), single crystal X-ray diffractometry, solid state nuclear magnetic resonance (NMR), infrared (IR) spectroscopy, Raman spectroscopy, and hot-stage optical microscopy.

The present invention is directed to a crystalline Form 1 polymorph of the p-toluenesulfonic acid salt of 1-((2S,5R)-5-((7H-pyrrolo[2,3-d]pyrimidin-4-yl)amino)-2-methylpiperidin-1-yl)prop-2-en-1-one and to a novel phosphoric acid salt of 1-((2S,5R)-5-((7H-pyrrolo[2,3-d]pyrimidin-4-yl)amino)-2-methylpiperidin-1-yl)prop-2-en-1-one. The invention is also directed to compositions, including pharmaceutical compositions, containing the Form 1 polymorph of the p-toluenesulfonic acid salt of 1-((2S,5R)-5-((7H-pyrrolo[2,3-d]pyrimidin-4-yl)amino)-2-methylpiperidin-1-yl)prop-2-en-1-one and those containing a novel phosphoric acid salt of 1-((2S,5R)-5-((7H-pyrrolo[2,3-d]pyrimidin-4-yl)amino)-2-methylpiperidin-1-yl)prop-2-en-1-one. The invention is further directed to processes for preparing the crystalline Form 1 polymorph of the p-toluenesulfonic acid salt of 1-((2S,5R)-5-((7H-pyrrolo[2,3-d]pyrimidin-4-yl)amino)-2-methylpiperidin-1-yl)prop-2-en-1-one and the novel phosphoric acid salt of 1-((2S,5R)-5-((7H-pyrrolo[2,3-d]pyrimidin-4-yl)amino)-2-methylpiperidin-1-yl)prop-2-en-1-one.

Because drug formulations, showing, for example, enhanced bioavailability or stability are consistently sought, there is an ongoing need for new or purer polymorphic forms of drug molecules. The Form 1 polymorph of the p-toluenesulfonic acid salt of 1-((2S,5R)-5-((7H-pyrrolo[2,3-d]pyrimidin-4-yl)amino)-2-methylpiperidin-1-yl)prop-2-en-1-one and the novel phosphoric acid salt of 1-((2S,5R)-5-((7H-pyrrolo[2,3-d]pyrimidin-4-yl)amino)-2-methylpiperidin-1-yl)prop-2-en-1-one described herein help meet these and other needs.

SUMMARY OF THE INVENTION

The present invention provides crystalline forms of the phosphoric acid salt and the p-toluenesulfonic acid salts of 1-((2S,5R)-5-((7H-pyrrolo[2,3-d]pyrimidin-4-yl)amino)-2-methylpiperidin-1-yl)prop-2-en-1-one and a manufacturing process and intermediates for preparation thereof. Form I of the p-toluenesulfonic acid salt of 1-((2S,5R)-5-((7H-pyrrolo[2,3-d]pyrimidin-4-yl)amino)-2-methylpiperidin-1-yl)prop-2-en-1-one is characterized by a powder X-ray diffraction pattern, solid state $^{13}C$ nuclear magnetic resonance spectra, Raman spectra and FT-IR spectra.

In another aspect, the present invention comprises a crystalline form of the p-toluenesulfonic acid salt of 1-((2S,5R)-5-((7H-pyrrolo[2,3-d]pyrimidin-4-yl)amino)-2-methylpiperidin-1-yl)prop-2-en-1-one having one or more characteristics selected from the group consisting of:

I) an X-ray powder diffraction pattern comprising: (a) one, two, three, four, five, or more than five peaks selected from the group consisting of the peaks in Table 1 in °2θ±0.2° 2θ; (b) one, two, three, four, five, or more than five peaks selected from the group consisting of the characteristic peaks in Table 1 in °2θ±0.2° 2θ; or (c) peaks at 2θ values essentially the same as shown in FIG. 1

II) a Raman spectrum comprising: (a) one, two, three, four, five, or more than five wavenumber ($cm^{-1}$) values selected from the group consisting of the values in Table 2 in $cm^{-1}$±2 $cm^{-1}$; (b) one, two, three, four, five, or more than five wavenumber ($cm^{-1}$) values selected from the group consisting of the characteristic values in Table 2 in $cm^{-1}$±2 $cm^{-1}$; or (c) wavenumber ($cm^{-1}$) values essentially the same as shown in FIG. 2;

III) a $^{13}C$ solid state NMR spectrum (ppm) comprising: (a) one, two, three, four, five, or more than five resonance (ppm) values selected from the group consisting of the values in Table 3 in ppm±0.2 ppm; (b) one, two, three, four, five, or more than five resonance (ppm) values selected from the group consisting of the characteristic values in Table 3 in ppm±0.2 ppm; or (c) resonance (ppm) values essentially the same as shown in FIG. 3;

IV) or a combination of any two, three or four of the foregoing embodiments (I)(a)-(c), (II)(a)-(c), (III)(a)-(c), or (IV)(a)-(b), provided they are not inconsistent with each other.

In another aspect, the present invention provides a crystalline form of the p-toluenesulfonic acid salt of 1-((2S,5R)-5-((7H-pyrrolo[2,3-d]pyrimidin-4-yl)amino)-2-methylpiperidin-1-yl)prop-2-en-1-one, according to any of the embodiments described herein, crystallized from a solvent system that may include 2-propanol, 2-propanol and tetrahydrofuran, methyl ethyl ketone/water, acetonitrile/EtOH, ethanol and n-butanol, ethanol, n-butanol, 2-propanol and N,N-dimethylformamide, and/or tetrahydrofuran.

In another aspect, the invention further provides a pharmaceutical composition comprising a crystalline form of the p-toluenesulfonic acid salt of 1-((2S,5R)-5-((7H-pyrrolo[2,3-d]pyrimidin-4-yl)amino)-2-methylpiperidin-1-yl)prop-2-en-1-one, according to any of the embodiments described herein, and a pharmaceutically acceptable carrier or excipient.

In another aspect, the present invention also provides a method of treating a disease in a mammal, comprising administering to a mammal in need thereof a therapeutically effective amount of the p-toluenesulfonic acid salt of 1-((2S,5R)-5-((7H-pyrrolo[2,3-d]pyrimidin-4-yl)amino)-2-methylpiperidin-1-yl)prop-2-en-1-one according to any of the embodiments described herein, or a pharmaceutical composition thereof.

In yet another aspect, the invention provides use of the p-toluenesulfonic acid salt of 1-((2S,5R)-5-((7H-pyrrolo[2,3-d]pyrimidin-4-yl)amino)-2-methylpiperidin-1-yl)prop-2-en-1-one according to any of the embodiments described herein, in the manufacture of a medicament for the treatment of rheumatoid arthritis, myositis, vasculitis, pemphigus, bullous pemphigoid, inflammatory bowel disease, Crohn's disease, ulcerative colitis, celiac disease, proctitis, eosinophilic gastroenteritis, mastocytosis, Alzheimer's disease, lupus, nephritis, systemic lupus erythematosus, psoriasis, eczema dermatitis, pruritus or other pruritic conditions, vitiligo, alopecia, autoimmune thyroid disorders, multiple sclerosis, major depression disorder, allergy, asthma, Sjogren's disease, Reiter's syndrome, polymyositis-dermatomyositis, systemic sclerosis, polyarteritis *nodosa*, Hashimoto's thyroiditis, autoimmune hemolytic anemia, autoimmune atrophic gastritis of pernicious anemia, autoimmune encephalomyelitis, autoimmune orchitis, Goodpasture's disease, autoimmune thrombocytopenia, sympathetic ophthalmia, myasthenia gravis, Graves' disease, primary biliary cirrhosis, chronic aggressive hepatitis, membranous glomerulopathy, organ transplant rejection, graft-versus-host disease, organ and cell transplant rejection, xenotransplantation, Cogan's syndrome, ankylosing spondylitis, Wegener's granulomatosis, autoimmune alopecia, Type I or juvenile onset diabetes, complications from diabetes, thyroiditis, chronic pulmonary obstructive disorder, acute respiratory disease, cachexia, cancer, alimentary/gastrointestinal tract cancer, colon cancer, liver cancer, skin cancer, mast cell tumor, squamous cell carcinoma, breast, mammary cancer, ovarian cancer, prostate cancer, leukemia, adult T cell leukemia activated B-cell like, diffuse large B cell lymphoma, kidney cancer, lung cancer, muscle cancer, bone cancer, bladder cancer, brain cancer, melanoma, oral or metastatic melanoma, Kaposi's sarcoma septic shock, cardiopulmonary dysfunction, acute myeloid leukemia, T cell acute lymphoblastic leukemia, multiple myeloma, myeloproliferative disorders, proliferative diabetic retinopathy, angiogenic-associated disorders, solid tumors, pancreatic cancer, brain tumors, gliomas, astrocytoma, oligodendroglioma, glioblastoma, acute CNS trauma, traumatic brain injury, encephalitis, stroke, spinal cord injury, epilepsy, seizures, chronic neuroinflammation associated with neurodegeneration, Parkinson's disease, Amyotropic Lateral Sclerosis, Huntington's disease, cerebral ischemia, fronto-temporal lobe dementia, neuropsychiatric disorders, schizophrenia, bipolar disorder, treatment-resistant depression, Post Traumatic Stress Disorder, anxiety, auto-antibodies-mediated encephalopathies, eye diseases, autoimmune diseases of the eye, keratoconjunctivitis, vernal conjunctivitis, uveitis, uveitis associated with Behcet's disease and lens-induced uveitis, keratitis, herpetic keratitis, conical keratitis, corneal epithelial dystrophy, keratoleukoma, ocular premphigus, Mooren's ulcer, scleritis, Grave's ophthalmopathy, Vogt-Koyanagi-Harada syndrome, keratoconjunctivitis sicca (dry eye), phlyctenule, iridocyclitis, sarcoidosis, endocrine ophthalmopathy, sympathetic ophthalmitis, allergic conjunctivitis, and ocular neovascularization.

DETAILED DESCRIPTION OF THE INVENTION

Figure 1:
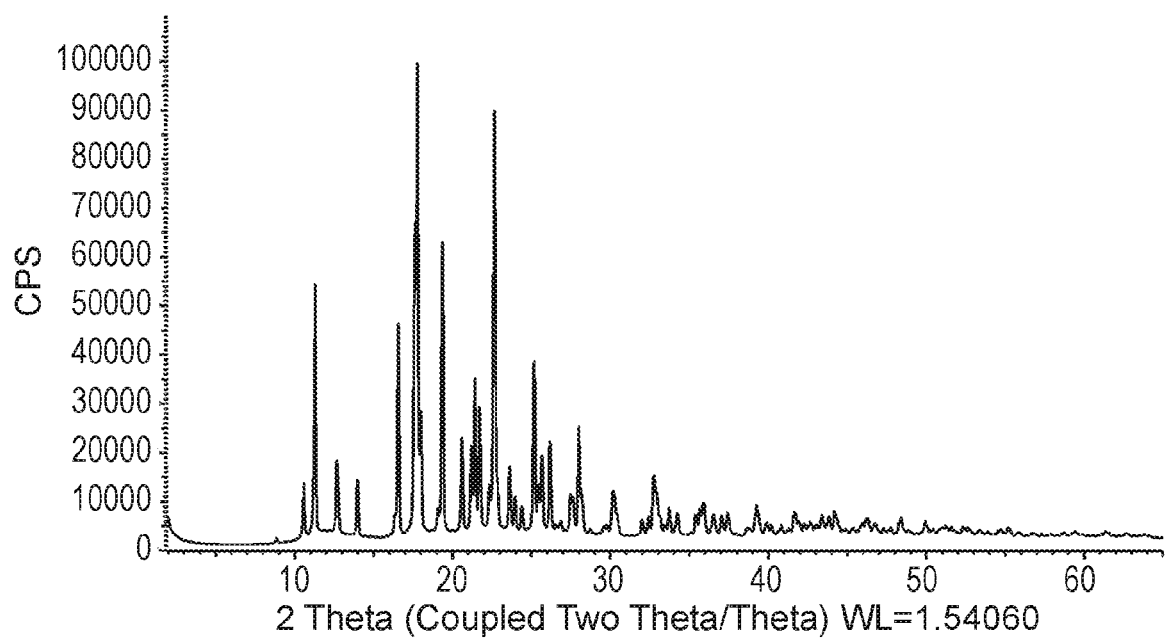
FIG. 1 depicts a X-ray powder diffraction pattern of the crystalline Form I of the p-toluenesulfonic acid salt of 1-((2S,5R)-5-((7H-pyrrolo[2,3-d]pyrimidin-4-yl)amino)-2-methylpiperidin-1-yl)prop-2-en-1-one prepared in accordance with the disclosed method.
Figure 2:
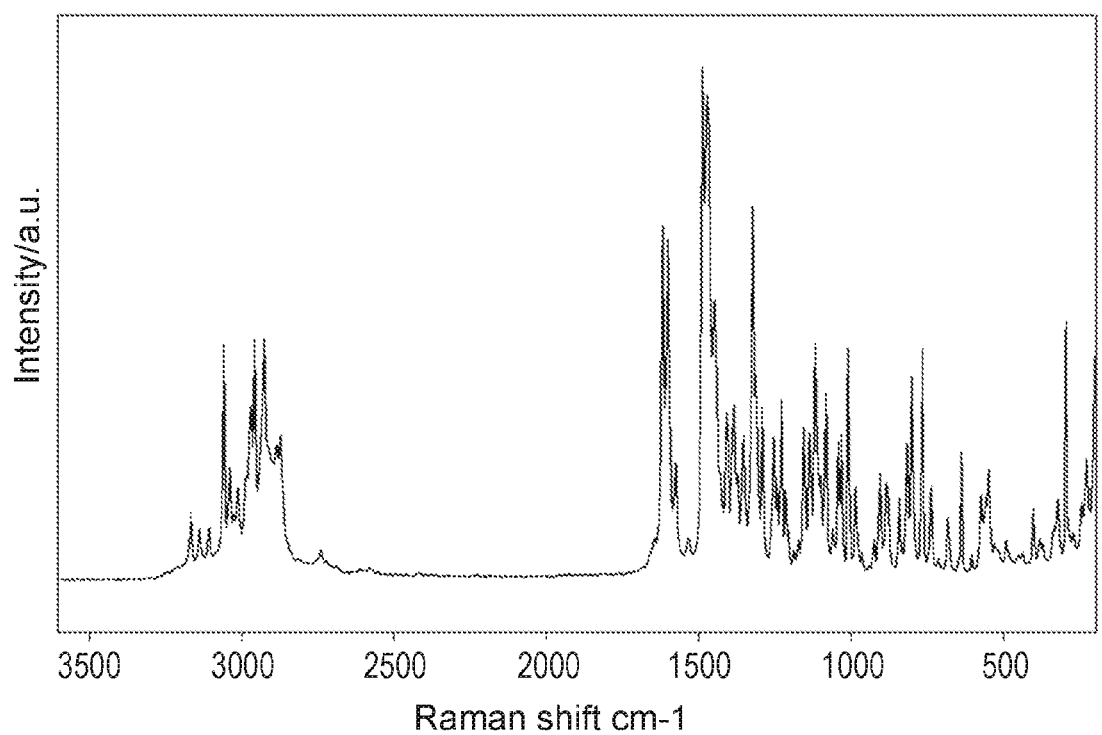
FIG. 2 depicts a Raman spectrum of the crystalline Form 1 of the p-toluenesulfonic acid salt of 1-((2S,5R)-5-((7H-pyrrolo[2,3-d]pyrimidin-4-yl)amino)-2-methylpiperidin-1-yl)prop-2-en-1-one prepared in accordance with the disclosed method.
Figure 3:
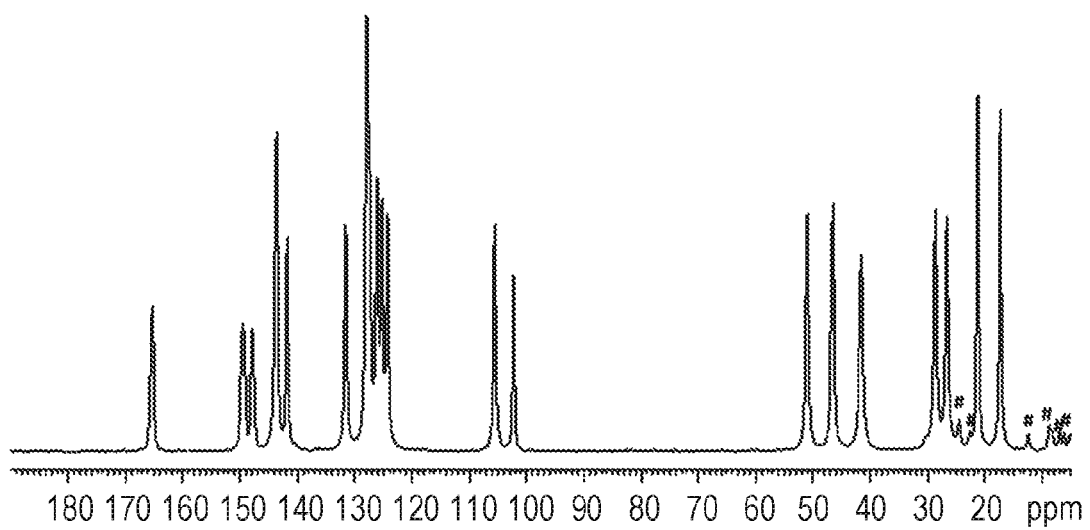
FIG. 3 depicts a solid state $^{13}C$ nuclear magnetic resonance spectrum of the crystalline Form I of the p-toluenesulfonic acid salt of 1-((2S,5R)-5-((7H-pyrrolo[2,3-d]pyrimidin-4-yl)amino)-2-methylpiperidin-1-yl)prop-2-en-1-one prepared in accordance with the disclosed method.

The present invention is directed to the p-toluenesulfonic acid salt of 1-((2S,5R)-5-((7H-pyrrolo[2,3-d]pyrimidin-4-yl)amino)-2-methylpiperidin-1-yl)prop-2-en-1-one and to a crystalline form of the p-toluenesulfonic acid salt thereof. The present invention is also directed to the phosphoric acid salt of 1-((2S,5R)-5-((7H-pyrrolo[2,3-d]pyrimidin-4-yl) amino)-2-methylpiperidin-1-yl)prop-2-en-1-one and to a crystalline form of the phosphoric acid salt thereof. The present invention is further directed to pharmaceutical compositions comprising the crystalline p-toluenesulfonic acid salt and to the phosphoric acid salt thereof, and to methods for preparing such forms. The invention is further directed to the use of the respective crystalline salts in the treatment of various diseases.

There are a number of analytical methods one of ordinary skill in the art in solid-state chemistry can use to analyze solid forms. The term "analyze" as used herein means to obtain information about the solid-state structure of solid forms. For example, X-ray powder diffraction is a suitable technique for differentiating amorphous solid forms from crystalline solid forms, distinguishing between crystalline forms and for characterizing and identifying crystalline solid forms of a compound. X-ray powder diffraction is also suitable for quantifying the amount of a crystalline solid form (or forms) in a mixture. In X-ray powder diffraction, X-rays are directed onto a powder comprising crystals and the intensity of the diffracted X-rays is measured as a function of angle between the X-ray source and the beam diffracted by the sample. The intensity of these diffracted X-rays can be plotted on a graph as peaks with the x-axis being twice the angle (this is known as the "2θ" angle) between the X-ray source and the diffracted X-rays and with the y-axis being the intensity of the diffracted X-rays. This graph is called an X-ray powder diffraction pattern or powder pattern. Different crystalline solid forms exhibit different powder patterns because the location of the peaks on the x-axis is a property of the solid-state structure of the crystal.

Such powder patterns, or portions thereof, can be used as an identifying fingerprint for a crystalline solid form. Thus, one could take a powder pattern of an unknown sample and compare that powder pattern with a reference powder pattern. A positive match would mean that the unknown sample is of the same crystalline solid form as that of the reference. One could also analyze an unknown sample containing a mixture of solid forms by adding and subtracting powder patterns of known compounds.

When selecting peaks in a powder pattern to characterize a crystalline solid form or when using a reference powder pattern to identify a form, one identifies a peak or collection of peaks in one form that are not present in the other solid forms.

The term "characterize" as used herein means to select an appropriate set of data capable of distinguishing one solid form from another. That set of data in X-ray powder diffraction consists of one or more X-ray diffraction peaks with positions and intensities specific to the solid form in question. Selecting which X-ray powder diffraction peaks define a particular form is said to characterize that form.

The term "identify" as used herein means taking a selection of characteristic data for a solid form and using those data to determine whether that form is present in a sample. In X-ray powder diffraction, those data are the x-axis positions of the one or more peaks characterizing the form in question as discussed above. For example, once one determines that a select number of X-ray diffraction peaks characterize a particular solid form, one can use those peaks to determine whether that form is present in a sample.

When characterizing and/or identifying crystalline solid forms of the same chemical compound with X-ray powder diffraction, it is often not necessary to use the entire powder pattern. A smaller subset of the entire powder pattern can often be used to perform the characterization and/or identification. By selecting a collection of peaks that differentiate the crystalline solid form from other crystalline solid forms of the compound, one can rely on those peaks to both characterize the form and to identify the form in, for example, an unknown mixture. Additional data can be added, such as from another analytical technique or additional peaks from the powder pattern, to characterize and/or identify the form should, for instance, additional polymorphs be identified later.

Due to differences in instruments, samples, and sample preparation, peak values are sometimes reported with the modifier "about" in front of the peak values. This is common practice in the solid-state chemical arts because of the variation inherent in peak values. A typical precision of the 2θ x-axis value of a peak in a powder pattern is on the order of plus or minus 0.2° 2θ. Thus, a powder diffraction peak that appears at "about 9.2° 2θ," means that the peak could be between 9.0° 2θ and 9.4° 2θ when measured on X-ray diffractometers having Cu Kα sources under most conditions. Variability in peak intensity is a result of how individual crystals are oriented in the sample container with respect to the external X-ray source (known as "preferred orientation"). This orientation effect does not provide structural information about the crystal. X-ray powder diffraction is just one of several analytical techniques one may use to characterize and/or identify crystalline solid forms. Spectroscopic techniques such as Raman (including microscopic Raman), infrared, and solid state NMR spectroscopies may be used to characterize and/or identify crystalline solid forms. These techniques may also be used to quantify the amount of one or more crystalline solid forms in a mixture and peak values can also be reported with the modifier "about" in front of the peak values. Atypical variability for a peak value associated with an FT-Raman and FT-Infrared measurement is on the order of plus or minus 2 cm$^{-1}$. A typical variability for a peak value associated with a $^{13}$C chemical shift is on the order of plus or minus 0.2 ppm for crystalline material.

In the first aspect, the present invention comprises a crystalline form having one or more characteristics selected from the group consisting of:

I) an X-ray powder diffraction pattern containing the following 2θ values measured using Cu K$_{α1}$ radiation (λ=1.54056 Å): 11.4, 14.1, 16.7, 17.9 and 21.6 2-theta positions ±0.2 2-theta.

II) a Raman spectrum containing the following wavenumber (cm$^{-1}$) values: 1617, 1601, 1040, 1032, 799 and 766 cm$^{-1}$±2 cm$^{-1}$.

III) an X-ray powder diffraction pattern containing the following 2θ values measured using Cu K$_{α1}$ radiation (λ=1.54056 Å): 11.4, 14.1, 16.7, 17.9 and 21.6 2-theta positions ±0.2 2-theta and a Raman spectrum containing the following wavenumber (cm$^{-1}$) values: 1617, 1601, 1040, 1032, 799 and 766 cm$^{-1}$±2 cm$^{-1}$.

IV) a $^{13}$C solid state NMR spectrum containing the following resonance (ppm) values: 17.3, 21.3, 28.7, 131.6, and 147.9±0.2 ppm.

V) an X-ray powder diffraction pattern containing the following 2θ values measured using Cu K$_{α1}$ radiation (λ=1.54056 Å): 11.4, 14.1, 16.7, 17.9 and 21.6 2-theta positions ±0.2 2-theta and a $^{13}$C solid state NMR spectrum containing resonance (ppm) values: 17.3, 21.3, 28.7, 131.6, and 147.9±0.2 ppm.

VI) a $^{13}$C solid state NMR spectrum containing the following resonance (ppm) values: 17.3, 21.3, 28.7, 131.6, and 147.9±0.2 ppm and a Raman spectrum containing the following wavenumber (cm$^{-1}$) values: 1617, 1601, 1040, 1032, 799 and 766 cm$^{-1}$±2 cm$^{-1}$.

VII) an X-ray powder diffraction pattern containing the following 2θ values measured using Cu K$_{α1}$ radiation (λ=1.54056 Å): 11.4, 14.1, 16.7, 17.9 and 21.6 2-theta positions ±0.2 2-theta, a Raman spectrum containing the following wavenumber (cm$^{-1}$) values: 1617, 1601, 1040, 1032, 799 and 766 cm$^{-1}$±2 cm$^{-1}$ and a $^{13}$C solid state NMR spectrum containing the following resonance (ppm) values: 17.3, 21.3, 28.7, 131.6, and 147.9±0.2 ppm.

The present invention also provides pharmaceutical compositions comprising the p-toluenesulfonic acid salt of 1-((2S,5R)-5-((7H-pyrrolo[2,3-d]pyrimidin-4-yl)amino)-2-methylpiperidin-1-yl)prop-2-en-1-one, and to methods for preparing such form, as well as pharmaceutical compositions thereof for use in medicine and for use in treating such diseases or conditions as rheumatoid arthritis, myositis, vasculitis, pemphigus, bullous pemphigoid, inflammatory bowel disease, Crohn's disease, ulcerative colitis, celiac disease, proctitis, eosinophilic gastroenteritis, mastocytosis, Alzheimer's disease, lupus, nephritis, systemic lupus erythematosus, psoriasis, eczema dermatitis, pruritus or other pruritic conditions, vitiligo, alopecia, autoimmune thyroid disorders, multiple sclerosis, major depression disorder, allergy, asthma, Sjogren's disease, Reiter's syndrome, polymyositis-dermatomyositis, systemic sclerosis, polyarteritis nodosa, Hashimoto's thyroiditis, autoimmune hemolytic anemia, autoimmune atrophic gastritis of pernicious anemia, autoimmune encephalomyelitis, autoimmune orchitis, Goodpasture's disease, autoimmune thrombocytopenia, sympathetic ophthalmia, myasthenia gravis, Graves' disease, primary biliary cirrhosis, chronic aggressive hepatitis, membranous glomerulopathy, organ transplant rejection, graft-versus-host disease, organ and cell transplant rejection, xenotransplantation, Cogan's syndrome, ankylosing spondylitis, Wegener's granulomatosis, autoimmune alopecia, Type I or juvenile onset diabetes, complications from diabetes, thyroiditis, chronic pulmonary obstructive disorder, acute respiratory disease, cachexia, cancer, alimentary/gastrointestinal tract cancer, colon cancer, liver cancer, skin cancer, mast cell tumor, squamous cell carcinoma, breast, mammary cancer, ovarian cancer, prostate cancer, leukemia, adult T cell leukemia activated B-cell like, diffuse large B cell lymphoma, kidney cancer, lung cancer, muscle cancer, bone cancer, bladder cancer, brain cancer, melanoma, oral or metastatic melanoma, Kaposi's sarcoma septic shock, cardiopulmonary dysfunction, acute myeloid leukemia, T cell acute lymphoblastic leukemia, multiple myeloma, myeloproliferative disorders, proliferative diabetic retinopathy, angiogenic-associated disorders, solid tumors, pancreatic cancer, brain tumors, gliomas, astrocytoma, oligodendroglioma, glioblastoma, acute CNS trauma, traumatic brain injury, encephalitis, stroke, spinal cord injury, epilepsy, seizures, chronic neuroinflammation associated with neurodegeneration, Parkinson's disease, Amyotropic Lateral Sclerosis, Huntington's disease, cerebral ischemia, fronto-temporal lobe dementia, neuropsychiatric disorders, schizophrenia, bipolar disorder, treatment-resistant depression, Post Traumatic Stress Disorder, anxiety, auto-antibodies-mediated encephalopathies, eye diseases, autoimmune diseases of the eye, keratoconjunctivitis, vernal conjunctivitis, uveitis, uveitis associated with Behcet's disease and lens-induced uveitis, keratitis, herpetic keratitis, conical keratitis, corneal epithelial dystrophy, keratoleukoma, ocular premphigus, Mooren's ulcer, scleritis, Grave's ophthalmopathy, Vogt-Koyanagi-Harada syndrome, keratoconjunctivitis sicca (dry eye), phlyctenule, iridocyclitis, sarcoidosis, endocrine ophthalmopathy, sympathetic ophthalmitis, allergic conjunctivitis, and ocular neovascularization, comprising the step of administering to a subject an effective amount of a composition comprising the p-toluenesulfonic acid salt of 1-((2S,5R)-5-((7H-pyrrolo[2,3-d]pyrimidin-4-yl)amino)-

2-methylpiperidin-1-yl)prop-2-en-1-one. The present invention also provides the use of such pharmaceutical compositions in the manufacture of a medicament for treating the diseases and conditions set forth above.

In another aspect, the present invention also provides a phosphoric acid salt of 1-((2S,5R)-5-((7H-pyrrolo[2,3-d]pyrimidin-4-yl)amino)-2-methylpiperidin-1-yl)prop-2-en-1-one and a crystalline form of the phosphoric acid salt of 1-((2S,5R)-5-((7H-pyrrolo[2,3-d]pyrimidin-4-yl)amino)-2-methylpiperidin-1-yl)prop-2-en-1-one.

The present invention also provides a process of making a p-toluenesulfonic acid salt of 1-((2S,5R)-5-((7H-pyrrolo[2,3-d]pyrimidin-4-yl)amino)-2-methylpiperidin-1-yl)prop-2-en-1-one, comprising stirring a solution of p-toluenesulfonic acid monohydrate and 1-((2S,5R)-5-((7H-pyrrolo[2,3-d]pyrimidin-4-yl)amino)-2-methylpiperidin-1-yl)prop-2-en-1-one dissolved in a suitable solvent. In a particular aspect, the invention provides a process, wherein the suitable solvent is either a mixture of methyl ethyl ketone and water or acetonitrile/ethanol.

The present invention further provides a process of making 1-((2S,5R)-5-((7H-pyrrolo[2,3-d]pyrimidin-4-yl)amino)-2-methylpiperidin-1-yl)prop-2-en-1-one, comprising reacting a compound have the structure:

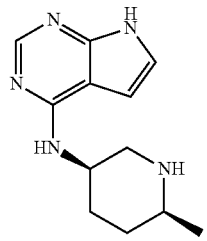 [SMILES: C[C@H]1CC[C@@H](Nc2ncnc3[nH]ccc23)CN1]

with a compound having the structure:

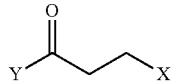

where X and Y are independently selected from a group consisting of chlorine, bromine and iodine under suitable basic conditions so as to form 1-((2S,5R)-5-((7H-pyrrolo[2,3-d]pyrimidin-4-yl)amino)-2-methylpiperidin-1-yl)prop-2-en-1-one. In certain aspects, the invention provides a process, wherein both X and Y are chlorine. In certain other aspects, the invention provides a process, wherein said basic conditions comprise an aqueous sodium or potassium hydroxide solution. In other aspects, the invention provides a process, further comprising forming the p-toluenesulfonic acid salt of 1-((2S,5R)-5-((7H-pyrrolo[2,3-d]pyrimidin-4-yl)amino)-2-methylpiperidin-1-yl)prop-2-en-1-one by reaction with p-toluenesulfonic acid under suitable conditions to result in said salt. In yet other aspects, the invention provides a process, wherein said suitable conditions comprise an aqueous solution of methyl ethyl ketone or t-amyl alcohol.

The present invention also provides a compound having the structure:

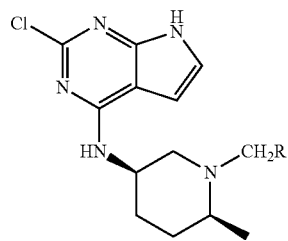

wherein R an aryl group selected from phenyl, toluyl, xylyl and pyridyl. In a particular aspect, the invention provides a compound, wherein R is phenyl.

The present invention also provides pharmaceutical compositions comprising the phosphoric acid salt of 1-((2S,5R)-5-((7H-pyrrolo[2,3-d]pyrimidin-4-yl)amino)-2-methylpiperidin-1-yl)prop-2-en-1-one. In a certain aspect, the invention provides said pharmaceutical composition, further comprising a pharmaceutically acceptable carrier. The present invention also provides methods for preparing the phosphate salt form. In particular aspect, the invention provides a process of making a phosphoric acid salt of 1-((2S,5R)-5-((7H-pyrrolo[2,3-d]pyrimidin-4-yl)amino)-2-methylpiperidin-1-yl)prop-2-en-1-one, comprising stirring a solution of phosphoric acid and 1-((2S,5R)-5-((7H-pyrrolo[2,3-d]pyrimidin-4-yl)amino)-2-methylpiperidin-1-yl)prop-2-en-1-one dissolved in a suitable solvent. In a certain aspect, the invention provides a process of preparation, wherein the suitable solvent is a mixture of methyl ethyl ketone and water.

The present invention also provides pharmaceutical compositions of the phosphate salt form for use in medicine and, in particular, for use in treating such diseases or conditions as rheumatoid arthritis, myositis, vasculitis, pemphigus, bullous pemphigoid, inflammatory bowel disease, Crohn's disease, ulcerative colitis, celiac disease, proctitis, eosinophilic gastroenteritis, mastocytosis, Alzheimer's disease, lupus, nephritis, systemic lupus erythematosus, psoriasis, eczema dermatitis, pruritus or other pruritic conditions, vitiligo, alopecia, autoimmune thyroid disorders, multiple sclerosis, major depression disorder, allergy, asthma, Sjogren's disease, Reiter's syndrome, polymyositis-dermatomyositis, systemic sclerosis, polyarteritis *nodosa*, Hashimoto's thyroiditis, autoimmune hemolytic anemia, autoimmune atrophic gastritis of pernicious anemia, autoimmune encephalomyelitis, autoimmune orchitis, Goodpasture's disease, autoimmune thrombocytopenia, sympathetic ophthalmia, myasthenia gravis, Graves' disease, primary biliary cirrhosis, chronic aggressive hepatitis, membranous glomerulopathy, organ transplant rejection, graft-versus-host disease, organ and cell transplant rejection, xenotransplantation, Cogan's syndrome, ankylosing spondylitis, Wegener's granulomatosis, autoimmune alopecia, Type I or juvenile onset diabetes, complications from diabetes, thyroiditis, chronic pulmonary obstructive disorder, acute respiratory disease, cachexia, cancer, alimentary/gastrointestinal tract cancer, colon cancer, liver cancer, skin cancer, mast cell tumor, squamous cell carcinoma, breast, mammary cancer, ovarian cancer, prostate cancer, leukemia, adult T cell leukemia activated B-cell like, diffuse large B cell lymphoma, kidney cancer, lung cancer, muscle cancer, bone cancer, bladder cancer, brain cancer, melanoma, oral or metastatic melanoma, Kaposi's sarcoma septic shock, cardiopulmonary dysfunction, acute myeloid leukemia, T cell acute lymphoblastic leukemia, multiple myeloma, myeloproliferative disorders, proliferative diabetic retinopathy, angiogenic-associated disorders, solid tumors, pancreatic cancer, brain tumors, gliomas, astrocytoma, oligodendroglioma, glioblastoma, acute CNS trauma, traumatic brain injury, encephalitis, stroke, spinal cord injury, epilepsy, seizures, chronic neuroinflammation associated with neurodegeneration, Parkinson's disease, Amyotropic Lateral Sclerosis, Huntington's disease, cerebral ischemia, fronto-temporal lobe dementia, neuropsychiatric disorders, schizophrenia, bipolar disorder, treatment-resistant depression, Post Traumatic Stress Disorder, anxiety, auto-antibodies-mediated encephalopathies, eye diseases, autoimmune diseases of the eye, keratoconjunctivitis, vernal conjunctivitis, uveitis, uveitis associated with Behcet's disease and lens-induced uveitis, keratitis, herpetic keratitis, conical keratitis, corneal epithelial dystrophy, keratoleukoma, ocular premphigus, Mooren's ulcer, scleritis, Grave's ophthalmopathy, Vogt-Koyanagi-Harada syndrome, keratoconjunctivitis sicca (dry eye), phlyctenule, iridocyclitis, sarcoidosis, endocrine ophthalmopathy, sympathetic ophthalmitis, allergic conjunctivitis, and ocular neovascularization, comprising the step of administering to a subject an effective amount of a composition comprising the phosphoric acid salt of 1-((2S,5R)-5-((7H-pyrrolo[2,3-d]pyrimidin-4-yl)amino)-2-methylpiperidin-1-yl)prop-2-en-1-one. The present invention also provides the use of such pharmaceutical compositions in the manufacture of a medicament for treating the diseases and conditions set forth above.

Methods of treating the diseases and syndromes listed herein are understood to involve administering to an individual in need of such treatment a therapeutically effective amount of the respective salts or crystalline forms of the invention, or a composition containing the same. As used herein, the term "treating" in reference to a disease is meant to refer to preventing, inhibiting and/or ameliorating the disease.

As used herein, the term "individual" or "patient," used interchangeably, refers to any animal, including mammals, preferably mice, rats, other rodents, rabbits, dogs, cats, swine, cattle, sheep, goats, horses, or primates, and most preferably humans. As used herein, the phrase "therapeutically effective amount" refers to the amount of active compound or pharmaceutical agent that elicits the biological or medicinal response in a tissue, system, animal, individual or human that is being sought by a researcher, veterinarian, medical doctor or other clinician, which includes one or more of the following:

(1) preventing the disease; for example, preventing a disease, condition or disorder in an individual that may be predisposed to the disease, condition or disorder but does not yet experience or display the pathology or symptomatology of the disease;

(2) inhibiting the disease; for example, inhibiting a disease, condition or disorder in an individual that is experiencing or displaying the pathology or symptomatology of the disease, condition or disorder (i.e., arresting or slowing further development of the pathology and/or symptomatology); and (3) ameliorating the disease; for example, ameliorating a disease, condition or disorder in an individual that is experiencing or displaying the pathology or symptomatology of the disease, condition or disorder (i.e., reversing the pathology and/or symptomatology).

Dosage and Formulation

The invention also includes pharmaceutical compositions of one or more of the presently disclosed salts or polymorphs, respectively, along with one or more pharmaceutically acceptable carriers, excipients, vehicles, etc.

The compounds of these teachings can be prepared by methods known in the art. The reagents used in the preparation of the compounds of these teachings can be either commercially obtained or can be prepared by standard procedures described in the literature. For example, compounds of the present invention can be prepared according to the methods illustrated in the following examples.

Variations, modifications, and other implementations of what is described herein will occur to those skilled in the art without departing from the spirit and the essential characteristics of the present teachings. Accordingly, the scope of the present teachings is to be defined not by the preceding illustrative description but instead by the following claims, and all changes that come within the meaning and range of equivalency of the claims are intended to be embraced therein.

Each of the printed publications, including but not limited to patents, patent applications, books, technical papers, trade publications and journal articles described or referenced in this specification are herein incorporated by reference in their entirety and for all purposes.

The description of this invention utilizes a variety of abbreviations well known to those skilled in the art, including the following:
aq.: aqueous
$CH_3CN$: Acetonitrile
DCM: Dichloromethane
DMF: N,N-Dimethylformamide
DMSO: Dimethylsulfoxide
EtOAc: Ethyl acetate
EtOH: Ethanol
FT-IR: Fourier Transform-Infrared
HOAc: Acetic acid
MeOH: Methanol
XPRD: X-ray powder diffraction
ss $^{13}C$ NMR: solid state $^{13}C$ nuclear magnetic resonance
THF: Tetrahydrofuran
TLC: Thin Layer Chromatography

EXAMPLES

The following non-limiting examples are presented merely to illustrate the present invention. The skilled person will understand that there are numerous equivalents and variations not exemplified but which still form part of the present teachings.

General. All commercially available materials and solvents were used as received, unless otherwise stated. All reactions were executed under nitrogen atmosphere. Reaction temperatures were measured internally, unless indicated otherwise. Achiral UPLC analyses were carried out on a Waters Acquity™ H-Class UPLC system using Waters HSS™ T3 column (2.1×100 mm, 1.8 μm); column temperature 45° C.; flow rate 0.65 mL/min; detection UV 210 nm; mobile phase: 0.1% MsOH in water (Solvent A), acetonitrile (Solvent B); Gradient elution (12 min.): 0-8.20 min. increasing solvent B from 2% to 50%, 8.20-9.00 min. increasing solvent B from 50% to 100%, 9.00-9.50 min. holding solvent B at 100%, 9.50-9.51 min. decreasing solvent B from 100% to 2%, 9.51-12.00 min. holding solvent A at 2%. Chiral SFC analyses were carried out on a Waters UPC$^2$ SFC system using Chiralcel™ OJ-H column (4.6×250 mm, 5 μm); column temperature 40° C.; flow rate 4.0 mL/min; detection UV 210 nm; back pressure 150 bar; mobile phase: $CO_2$ (Solvent A), 75:25 acetonitrile/MeOH+0.1% TFA+

0.1% isopropylamine (Solvent B); Gradient elution (15 min.): 0-11.0 min. increasing solvent B from 5% to 30%, 11.0-11.1 min. holding solvent B at 30%, 11.1-11.2 min. decreasing solvent B from 30% to 5%, 11.2-12.0 min. holding solvent B at 5%.

Example 1

Preparation of 1-((2S,5R)-5-((7H-Pyrrolo[2,3-d] pyrimidin-4-yl)amino)-2-meth-ylpiperidin-1-yl) prop-2-en-1-one p-Toluenesulfonic Acid Salt (Form 1)

(A) To a 50 mL EasyMax™ flask equipped with an overhead stirrer, p-toluenesulfonic acid monohydrate (7.01 mmol, 1.35 g), methyl ethyl ketone (10.0 mL) and water (0.30 mL) were added. The solution was stirred at 22° C. for 5 min. A solution of 1-((2S,5R)-5-((7H-pyrrolo[2,3-d]pyrimidin-4-yl)amino)-2-methylpiperidin-1-yl)prop-2-en-1-one (7.01 mmol, 2.00 g) in methyl ethyl ketone (10.0 mL) was added slowly via addition funnel over 20 min. The slurry was stirred at 22° C. for 30 min. Methyl ethyl ketone (10.0 mL) was added slowly via addition funnel over 15 min. The slurry was stirred at 22° C. for 60 min. and then filtered. The solid was washed with methyl ethyl ketone (2×3 mL) and dried in a vacuum oven (30° C.) for 16 hours. 1-((2S,5R)-5-((7H-Pyrrolo[2,3-d]pyrimidin-4-yl)amino)-2-methylpiperidin-1-yl)prop-2-en-1-one p-toluene-sulfonic acid salt (Form 1) (5.81 mmol, 2.66 g) was obtained as a white sandy powder in 82.9% yield. The typical purity was above 99%.

(B) A solution of p-toluenesulfonic acid monohydrate (2.66 g, 13.8 mmol) in methyl ethyl ketone (7.2 mL) was added to a stirred solution of 1-((2S,5R)-5-((7H-pyrrolo[2,3-d]pyrimidin-4-yl)amino)-2-methylpiperidin-1-yl)prop-2-en-1-one (3.60 g, 12.5 mmol) in methyl ethyl ketone (22.5 mL) and water (1.56 mL) at 22° C. The seed of PF-06651600-15 (89 mg) was added and the mixture was stirred at 22° C. for 4 hours. methyl ethyl ketone (48 mL) was then slowly added over a period of 1 hour. The slurry was stirred at 22° C. for 18 hours and then filtered. The cake was washed with methyl ethyl ketone (15 mL) and then dried under vacuum at 40° C. for 4 hours. 1-((2S,5R)-5-((7H-Pyrrolo[2,3-d]pyrimidin-4-yl)amino)-2-methylpiperidin-1-yl)prop-2-en-1-one p-toluenesulfonic acid salt Form 1 (4.95 g, 10.8 mmol) was obtained as a white solid in 86% yield.

Example 2

Preparation of 1-((2S,5R)-5-((7H-Pyrrolo[2,3-d] pyrimidin-4-yl)amino)-2-meth-ylpiperidin-1-yl) prop-2-en-1-one Phosphoric Acid Salt (Form A)

A solution of 1-((2S,5R)-5-((7H-Pyrrolo[2,3-d]pyrimidin-4-yl)amino)-2-meth-ylpiperidin-1-yl)prop-2-en-1-one (18.00 g, 63.1 mmol) in MEK (133 mL) and water (10.8 mL) was added slowly over a period of 10 minutes to a stirred solution of 85% phosphoric acid (8.00 g, 69.4 mmol) in acetone (72 mL) and water (18 mL) at 22° C. The seed of 1-((2S,5R)-5-((7H-pyrrolo[2,3-d]pyrimidin-4-yl)amino)-2-meth-ylpiperidin-1-yl)prop-2-en-1-one (200 mg) was added when 50 mL of 1-((2S,5R)-5-((7H-pyrrolo[2,3-d]pyrimidin-4-yl)amino)-2-meth-ylpiperidin-1-yl)prop-2-en-1-one solution was added. The slurry was stirred at 22° C. for 4 hours and then filtered. The cake was washed with 15:1 v/v MEK/water (48 mL) and then dried under vacuum at 50° C. for 16 hours. 1-((2S,5R)-5-((7H-pyrrolo[2,3-d]pyrimidin-4-yl)amino)-2-meth-ylpiperidin-1-yl)prop-2-en-1-one phosphate salt Form A (21.30 g, 55.6 mmol) was obtained as a white solid in 88% yield.

Preparations

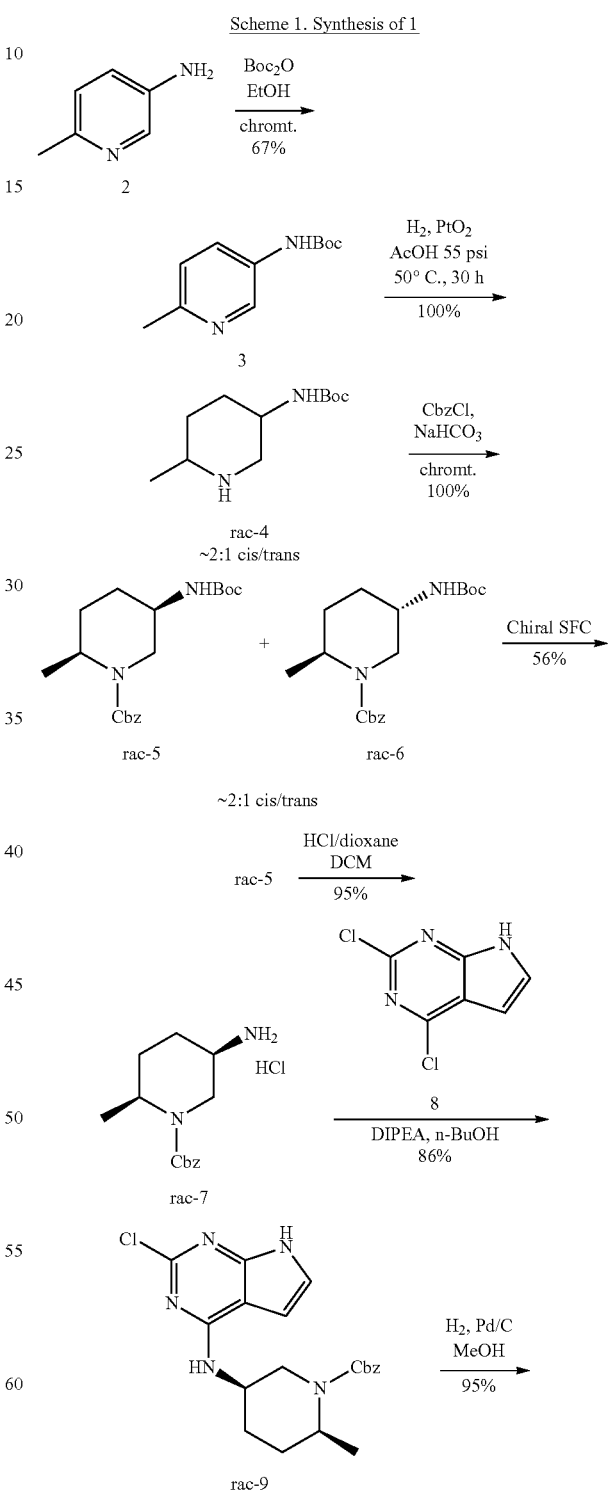

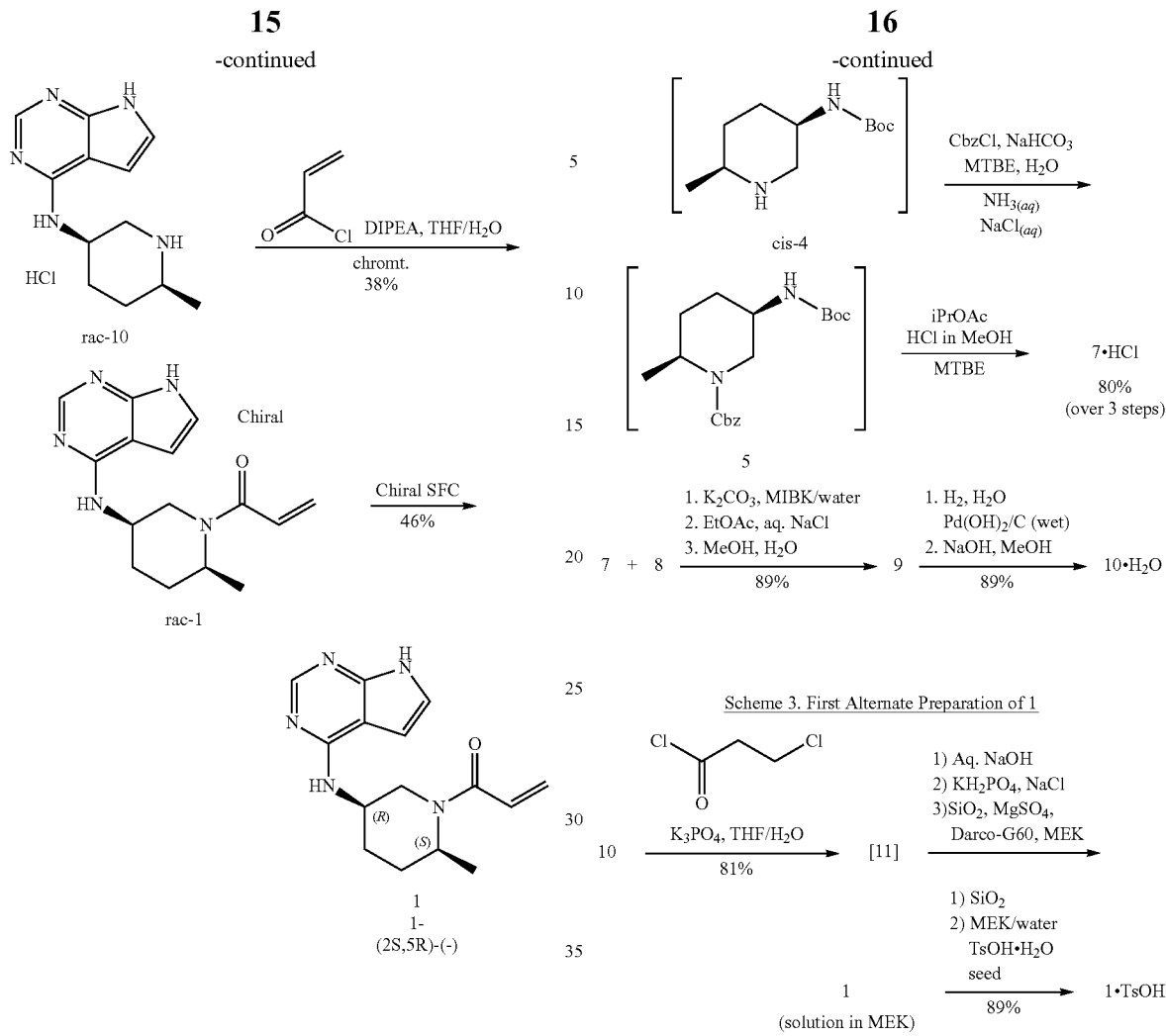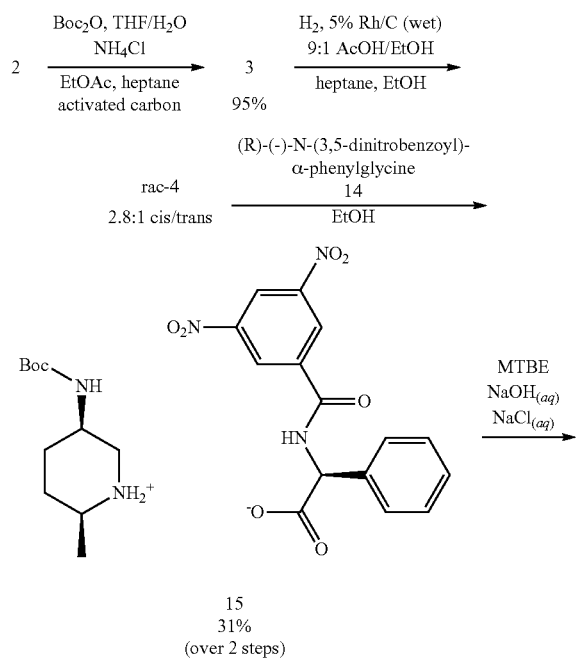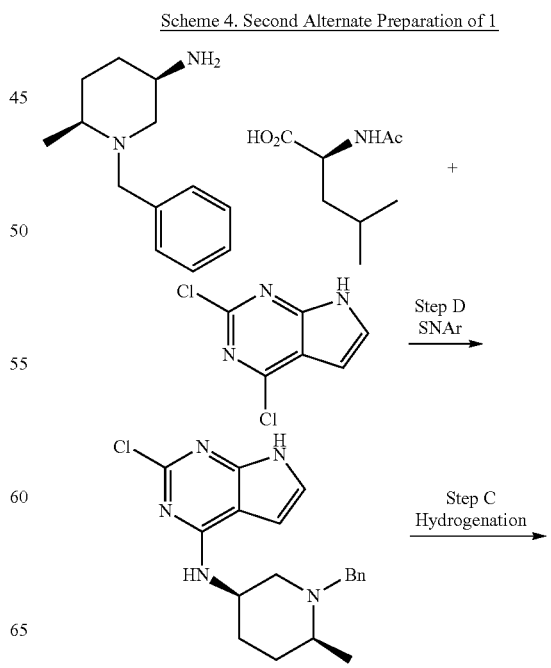

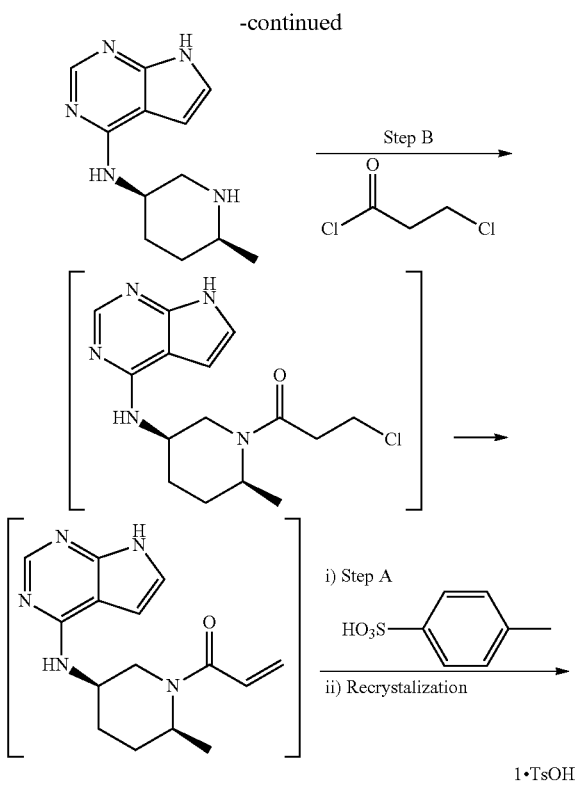

Preparation 1 tert-Butyl (6-methylpyridin-3-yl)carbamate (3). To a 3000 L reactor was charged 2 (72.00 kg, 665.8 mol) and THF (660 kg). A solution of NH$_4$Cl (1.07 kg, 20 mol) in water (72 kg, 4000 mol) was added. The mixture was heated to 57° C. and Di-t-butyl dicarbonate (220.0 kg, 1003 mol) was added slowly with rinse of THF (45 kg) while maintaining the temperature between 55-60° C. The mixture was stirred at 55-60° C. for 10 h. Upon reaction completion, the slurry was cooled to 20° C. and ethyl acetate (654 kg) and water (367 kg) were added. The organic phase was separated, washed by water (2×360 kg) and stirred with active carbon (22 kg) for 5 h. The mixture was filtered through a layer of diatomaceous earth (22 kg) with THF rinse and the filtrates were concentrated under vacuum at <40° C. to a residual volume of ~370 L. n-Heptane (500 kg) was added slowly over 1 h and the resulting slurry was cooled to 20° C. and stirred for 2 h. The solid was collected by centrifuge with an n-heptane wash (420 kg), then dried at 45° C. under vacuum for 20 h to give 3 (131.15 kg, 629.7 mol) as a white powder in 94.5% yield. HPLC purity: 99.9%. $^1$H NMR (400 MHz, DMSO-d6): δ ppm 9.42 (brs, 1H), 8.48 (d, J=1.9 Hz, 1H), 7.75 (d, J=8.6 Hz, 1H), 7.13 (d, J=8.6 Hz, 1H), 2.38 (s, 3H), 1.49 (s, 9H). $^{13}$C NMR (100 MHz, DMSO-d$_6$): δ ppm 153.34, 151.56, 139.75, 134.13, 126.10, 123.09, 79.87, 28.56, 23.70. HRMS (ESI) m/z: calculated for C$_{11}$H$_{17}$N$_2$O$_2$ [M+H]$^+$ 209.1290; observed 209.1285.

Preparation 2 tert-Butyl (6-methylpiperidin-3-yl)carbamate (rac-4). To a 3000 L reactor was charged 3 (137.0 kg, 667.8 mol), ethanol (988 kg) and acetic acid (139 kg). The reactor was purged with nitrogen three times and 5 wt % Rhodium on carbon (wet, 27.4 kg, 20 wt % loading relative to 3) was added. The reactor was purged with nitrogen three times and then with hydrogen three times. The hydrogen pressure was adjusted to 0.34-0.38 MPa and the reactor temperature was adjusted to 47° C. The mixture was stirred at 45-60° C. under hydrogen pressure at 0.34-0.38 MPa for 10 h. Upon reaction completion, the reactor was cooled to 20° C. and flushed with nitrogen. The mixture was filtered through a layer of diatomaceous earth (20 kg) with an ethanol rinse (1320 kg) and the filtrates were concentrated under vacuum at <50° C. to a residual volume of ~350 L. n-Heptane (571 kg) was added and the mixture was concentrated under vacuum at <50° C. to a residual volume of ~350 L. This operation was repeated twice until the residual acetic acid<8.0%. Ethanol (672 kg) was added and the mixture was concentrated under vacuum at <50° C. to a residual volume of ~350 L. This operation was repeated twice until the residual n-heptane was <0.2% and water was <0.2%. Ethanol (889 kg) was added and the solution (1254 kg) was transferred to drums for use in the subsequent classical resolution step. Achiral HPLC assay indicated that the solution contained 10.8 wt % of the total reduced product (rac-4) in 96% mass recovery and chiral SFC showed that the solution contained 36.3% of the desired stereoisomer cis-4.

Preparation 3 tert-Butyl ((3R,6S)-6-methylpiperidin-3-yl)carbamate (R)-2-(3,5-dinitrobenzamido)-2-phenylacetic acid salt (15). To a 2000 L reactor (R1) was charged rac-4 as a 10.8 wt % solution in ethanol (620.5 kg, ~312.7 mol. of all 4 isomers). The solution was concentrated under vacuum at <45° C. to a residual volume of ~210 L and then cooled to 20° C. To a 3000 L reactor (R2) was charged (R)-2-(3,5-dinitrobenzamido)-2-phenylacetic acid 14 (47.0 kg, 136.1 mol) and ethanol (1125 kg). With high speed agitation, reactor R2 was heated to 70° C., stirred at 68-70° C. for ~2 h to dissolve all solid 14, and then seeded with crystalline 15 (11 g). The solution containing 4 in reactor R1 was slowly transferred to reactor R2 over 30 min with ethanol rinse (160 kg). Reactor R2 was stirred at ~74° C. for 3 h and then cooled to 22° C. with a linear cooling rate over a period of 5 h and stirred for 16 h. The solid was collected by centrifuge with ethanol wash (2×200 kg). The wet cake (with 97.1% e.e.) was charged back to reactor R2. The slurry was heated to 74° C. and the mixture was stirred for 17 h. The mixture was then cooled to 22° C. with a linear cooling rate over a period of 5 h and stirred for 4 h. The solid was collected by centrifuge with ethanol wash (2×200 kg) and dried at 35° C. under vacuum for 25 h to give 15 (56.05 kg, 100.2 mol) as a white powder in 30.7% yield over 2 steps. Chiral HPLC purity: 99.1%. $^1$H NMR (400 MHz, DMSO-d$_6$): δ ppm 9.46 (d, J=7.0 Hz, 1H), 9.07 (d, J=2.2 Hz, 2H), 8.96 (t, J=2.2 Hz, 1H), 7.49 (d, J=7.3 Hz, 2H), 7.30 (t, J=7.3 Hz, 2H), 7.23 (t, J=7.3, 1H), 7.11 (m, 1H), 5.31 (d, J=7.0 Hz, 1H), 3.66 (m, 1H), 2.98 (m, 3H), 1.63 (m, 2H), 1.45 (m, 2H), 1.40 (s, 9H), 1.11 (d, J=6.7 Hz, 3H). $^{13}$C NMR (100 MHz, DMSO-d$_6$): δ ppm 172.71, 161.71, 155.42, 148.51, 141.27, 137.70, 128.29, 128.25, 128.02, 127.05, 121.12, 78.49, 59.74, 50.66, 46.29, 43.34, 28.66, 26.88, 26.11, 18.60.

Preparation 4

Benzyl (2S,5R)-5-amino-2-methylpiperidine-1-carboxylate hydrochloride (7·HCl)—telescoped process. To a 2000 L reactor was charged 15 (70.0 kg, 125 mol) and MTBE (500 kg). The mixture was cooled to 12° C. and 6.9 wt % aqueous NaOH solution (378 kg, 652 mol) was added slowly while maintaining the temperature between 10-25° C. The mixture was stirred at 18° C. for 1 h. The organic phase was separated and washed with 3.8 wt % aqueous NaOH solution (2×221 kg) and then 25 wt % aqueous NaCl solution (2×220 kg). The organic layer (containing the free base cis-4) was concentrated under vacuum at <40° C. to a residual volume of ~300 L and then cooled to 20° C. NaHCO$_3$ (53 kg, 632 mol) and water (200 kg) were added and the mixture was cooled to 7° C. Benzyl chloroformate (32.30 kg, 189.3 mol) was added slowly while maintaining the temperature between 5-20° C. The mixture was stirred at 17° C. for 20 h. Upon reaction completion, the mixture was cooled to 12° C., 25 wt % aqueous ammonium hydroxide solution (79 kg, 1160 mol) was added slowly while maintaining the temperature between 10-20° C., and the mixture was stirred at 15° C. for 1 h. The organic phase was separated and washed with 25 wt % aqueous NaCl solution (3×90 kg). The organic layer (containing 5) was concentrated under vacuum at <45° C. to a residual volume of ~150 L. Isopropyl acetate (310 kg) was added and the mixture was concentrated under vacuum at <45° C. to a residual volume of ~150 L. This operation was repeated twice to meet the criteria of water<0.1% (by KF). Isopropyl acetate (130 kg) was then added and the mixture was cooled to −3° C. 4-5N HCl in methanol (181 kg, ~730 mol) was added slowly while maintaining the temperature between −5 to 5° C., and the mixture was stirred at 3° C. for 12 h. Upon reaction completion, the mixture was cooled to −3° C. and MTBE (940 kg) was added slowly while maintaining the temperature between −5 to 5° C. The resulting slurry was stirred at 3° C. for 3 h. The solid was collected by centrifuge with MTBE washes (4×70 kg), and then dried at 45° C. under vacuum for 20 h to give 7·HCl (28.60 kg, 100.4 mol) as a white powder in 80.3% yield. Achiral HPLC purity: 100%. Chiral SFC purity: 99.8% e.e. $^1$H NMR (400 MHz, DMSO-d$_6$): δ ppm 8.36 (brs, 3H), 7.37 (m, 5H), 5.09 (s, 2H), 4.31 (m, 1H), 4.16 (d, J=8.2 Hz, 1H), 3.00 (m, 2H), 1.82 (m, 2H), 1.59 (m, 2H), 1.11 (d, J=7.0 Hz, 3H). $^{13}$C NMR (100 MHz, DMSO-d$_6$): δ ppm 154.71, 137.24, 128.92, 128.34, 128.00, 66.89, 47.20, 45.66, 40.68, 28.16, 23.02, 15.67. HRMS (ESI) m/z: calculated for C$_{14}$H$_{20}$N$_2$O$_2$ [M+H]$^+$ 249.1603; observed 249.1598.

Preparation 5

Benzyl (2S,5R)-5-((2-chloro-7H-pyrrolo[2,3-d]pyrimidin-4-yl)amino)-2-methyl-piperidine-1-carboxylate (9). To a 2000 L reactor was charged 7·HCl (88.6 kg, 311.12 mol), 8 (56.0 kg, 298 mol), K$_2$CO$_3$ (133.0 kg, 962.3 mol), water (570 kg) and MIBK (101 kg). The mixture was heated to 90° C. and stirred at this temperature for 22 h. Upon reaction completion, the mixture was cooled to 56° C. and ethyl acetate (531 kg) was added. After cooling the mixture to 22° C., the organic phase was separated, washed with water (570 kg) and concentrated under vacuum at <40° C. to a residual volume of ~220 L. Methanol (360 kg) was added slowly over a period of 1 h and the mixture concentrated under vacuum at <50° C. to a residual volume of ~220 L. This operation was repeated three times until residual MIBK reached <5 wt %. Methanol (270 kg) was added, followed by seeding with 9 (120 g). The mixture was stirred at 22° C. for >4 h and water (286 kg) was added slowly over 4 h. The slurry was stirred for 10 h and the solid was then collected by centrifuge. The wet cake (165.6 kg) was charged back to a clean reactor and water (896 kg) was added. The slurry was heated to 55° C. and stirred at this temperature for 7 h; and then cooled to 22° C. and stirred at this temperature for 2 h. The solid was collected by centrifuge with water wash (3×170 kg) and dried at 55° C. under vacuum for 20 h to give 9 (106.62 kg, 266.6 mol) as a white powder in 89.5% yield. Achiral HPLC purity: 99.7%. $^1$H NMR (400 MHz, DMSO-d$_6$): δ ppm 11.71 (brs, 1H), 7.72 (d, J=7.9 Hz, 1H), 7.38 (m, 5H), 7.10 (s, 1H), 6.57 (d, J=2.7 Hz, 1H), 5.11 (m, 2H), 4.39 (m, 1H), 4.17 (m, 1H), 4.01 (m, 1H), 3.36 (s, 2H), 2.77 (m, 1H), 1.73-1.81 (m, 4H), 1.16 (d, J=6.6 Hz, 3H). $^{13}$C NMR (100 MHz, DMSO-d$_6$): δ ppm 156.65, 154.74, 153.04, 151.31, 137.43, 128.89, 128.27, 127.96, 122.13, 101.65, 99.51, 66.75, 49.10, 47.32, 45.64, 42.98, 29.05, 25.08. HRMS (ESI) m/z: calculated for C$_{20}$H$_{22}$ClN$_5$O$_2$[M+H]$^+$ 400.1540; observed 400.1535.

Preparation 6

N-((3R,6S)-6-methylpiperidin-3-yl)-7H-pyrrolo[2,3-d]pyrimidin-4-amine monohydrate (10·H$_2$O) To a 1600 L reactor was charged water (570 kg). The reactor was purged with nitrogen three times. 10% Pd(OH)$_2$/C (wet, 3.2 kg) and 9 (53.34 kg, 133.2 mol) were added with water rinses (2×55 kg). The reactor was purged with nitrogen three times and then with hydrogen three times. The hydrogen pressure was adjusted to 0.34-0.38 MPa and the reactor temperature was adjusted to 77° C. The mixture was stirred at 75-80° C. under a hydrogen pressure of 0.34-0.38 MPa for 10 h. Upon reaction completion, the reactor was cooled to 20° C. and purged with nitrogen. The mixture was filtered through a layer of diatomaceous earth (8 kg) with a water rinse (460 kg), and the filtrates were transferred to a 3000 L reactor. Methanol (260 kg) was added, followed by slow addition of 50 wt % aqueous sodium hydroxide (12.0 kg, 150 mol) while maintaining the temperature between 15-25° C. The slurry was heated to 55° C. and stirred for 2 h; then cooled to 22° C. and stirred for 10 h. The solid was collected by centrifuge with a 10:1 water/methanol wash (3×110 kg) and then dried at 55° C. under vacuum for 20 h to give 10·H$_2$O (30.90 kg, 266.6 mol) as a white powder in 89.1% yield. Achiral HPLC purity: 99.7%. Chiral SFC purity: 99.8% e.e. $^1$H NMR (400 MHz, DMSO-d$_6$): δ ppm 11.48 (brs, 1H), 8.08 (s, 1H), 7.07 (s, 1H), 6.85 (d, J=7.3 Hz, 1H), 6.64 (s, 1H), 4.16 (m, 1H), 3.35 (brs, 2H), 2.96 (d, J=12.7 Hz, 1H), 2.82 (d, J=12.7 Hz, 1H), 2.67 (m, 1H), 2.04 (brs, 1H), 1.92 (m, 1H), 1.63 (m, 1H), 1.44 (m, 1H), 1.33 (m, 1H), 1.03 (d, J=6.2 Hz, 3H). $^{13}$C NMR (100 MHz, DMSO-d$_6$): δ ppm 155.95, 151.87, 150.74, 121.20, 102.97, 99.20, 51.27, 49.94, 44.78, 29.97, 28.69, 22.35. HRMS (ESI) m/z: calculated for C$_{12}$H$_{17}$N$_5$[M+H]$^+$ 232.1562; observed 232.1558.

Preparation 7

1-((2S,5R)-5-((7H-pyrrolo[2,3-d]pyrimidin-4-yl)amino)-2-methylpiperidin-1-yl)prop-2-en-1-one (1). To a 100 L reactor was charged water (18.0 L), 10·H$_2$O (3.60 kg, 14.4 mol) and THF (36.0 L). The mixture was heated to 53° C. and stirred for 15 min to dissolve all the solids. The solution was then cooled to 18° C. and K$_3$PO$_4$ (6.38 kg, 30.1 mol) was added. The mixture was stirred at 18° C. for 10 min to dissolve all the solids, and then cooled to 10° C. 3-Chloropropionyl chloride (2.20 kg, 17.3 mol) was added while maintaining the temperature<20° C. The mixture was then stirred at 20° C. for 2 h. Upon reaction completion, 2 N aqueous NaOH solution (23.50 kg, 43.76 mol) was added while maintaining the temperature<25° C. The mixture was stirred at 22° C. for >12 h until the elimination reaction was complete (11<0.2%). KH$_2$PO$_4$ (10.32 kg, 75.8 mol) was added and the mixture was stirred at 20° C. for 10 min. The organic phase was separated and then washed with 23.5 wt % aqueous NaCl solution (2×8.5 kg). The isolated organic phase was concentrated under vacuum at <30° C. to a residual volume of ~10 L, whereupon MEK (39.6 L) was added. This operation was repeated once or twice until residual THF was <1% and water was <2%. MgSO$_4$ (0.96 kg), Silica gel (4.90 kg) and Darco™ G-60 (0.48 kg) were added to the MEK solution, and the mixture was stirred at 20° C. for 1 h, then filtered through a layer of Diatomaceous Earth with a MEK rinse (76 L). The combined filtrates were concentrated under vacuum at <30° C. to a residual volume of ~8 L. The concentration of the residual solution was measured by qNMR, and the solution was transferred to a container with a rinse using the calculated amount of MEK to adjust the final concentration to 30 wt %. Thus, a 30 wt % solution of 1 in MEK (11.09 kg, 11.66 mol of 1) with 98.7% purity was obtained in 81% yield, which was stored in a cold room (2-8° C.) for the next step.

Preparation 8

1-((2S,5R)-5-((7H-pyrrolo[2,3-d]pyrimidin-4-yl)amino)-2-methylpiperidin-1-yl)prop-2-en-1-one p-toluenesulfonate (1·TsOH). To a 20 L reactor was charged a 30 wt % solution of 1 in MEK (9.80 kg, 10.30 mol of 1) and silica gel (0.74 kg). The mixture was stirred at 22° C. for 15 min and filtered through a 0.45 micron Teflon cartridge filter with a MEK rinse (7.89 kg, 9.8 L), collecting in a 100 L reactor. Water (1.27 L) was added, followed by a solution of p-toluenesulfonic acid monohydrate (2.18 kg, 11.3 mol) in MEK (4.75 kg, 5.9 L) with a MEK rinse (3.14 kg, 3.9 L), followed by the addition of 1·TsOH seed (188 g, 0.41 mol). The mixture was stirred at 22° C. for 4 h to form a slurry and MEK (31.56 kg, 39.2 L) was added slowly over a period of 3 h. The slurry was stirred at 22° C. for an additional 2 h and then filtered. The cake was washed with MEK (4.02 kg, 5 L) and then dried at 50° C. under vacuum for 10 h to give 1·TsOH (4.41 kg, 9.64 mol) as a white powder in 89.6% yield (accounting for the amount of seed charged). Achiral HPLC purity: 99.6% with 0.22% of dimer 15. Chiral SFC purity: >99.7%. m.p. 199° C. Rotomers observed for NMR spectroscopies. $^1$H NMR (400 MHz, DMSO-d$_6$): δ ppm 12.68 (brs, 1H), 9.22 (brs, 1H), 8.40 (s, 1H), 7.50 (d, J=8.2 Hz, 2H), 7.45 (m, 1H), 7.12 (d, J=8.2 Hz, 2H), 6.94 (d, J=1.2 Hz, 1H), 6.84 (m, 1H), 6.13 (m, 1H), 5.70 (m, 1H), 4.81 (m, 0.5H), 4.54 (m, 0.5H), 4.41 (m, 0.5H), 4.12 (m, 0.5H), 3.99 (m, 1H), 3.15 (m, 0.5H), 2.82 (m, 0.5H), 2.29 (s, 3H), 1.91-1.72 (m, 4H), 1.24-1.17 (m, 3H). $^{13}$C NMR (100 MHz, DMSO-d6): δ ppm 165.52, 165.13, 150.50, 145.64, 143.06, 138.48, 129.51, 129.24, 128.67, 127.99, 127.73, 125.97, 125.02, 102.30, 49.53, 48.92, 47.27, 43.83, 42.96, 29.37, 28.41, 25.22, 21.28, 16.97, 15.51. HRMS (ESI) m/z: calculated for $C_{15}H_{20}N_5O$ [M+H]$^+$ 286.1668; observed 286.1692.

Comparative Example

Preparation of 1-((2S,5R)-5-((7H-Pyrrolo[2,3-d]pyrimidin-4-yl)amino)-2-methyl-piperidin-1-yl) prop-2-en-1-one Malonic Acid Salt (Form 1)

A 250 mL round bottom flask was charged with 1-((2S,5R)-5-((7H-pyrrolo[2,3-d]pyrimidin-4-yl)amino)-2-methylpiperidin-1-yl)prop-2-en-1-one (4.10 g, 14.4 mmol), MEK (Methyl Ethyl Ketone (15.0 mL/g, 687 mmol, 49.5 g, 61.5 mL)). To the solution, malonic acid (0.950 equiv. 13.7 mmol, 1.42 g) was added in one portion. The mixture was heated to 50° C. and stirred at 50° C. for 15 min. The heating was turned off and the slurry was stirred for 16 hours. The resulting white slurry was filtered. The filter cake was washed with MEK (2×5 mL) and dried in a vacuum oven (40° C.) for 2 hours give 1-((2S,5R)-5-((7H-pyrrolo[2,3-d]pyrimidin-4-yl)amino)-2-methylpiperidin-1-yl)prop-2-en-1-one malonic acid salt (Form 1) (4.48 g, 11.5 mmol, 4.48 g, 80.1% Yield) as white powder.

Instrument and Analysis Methods:

Powder X-Ray Diffraction:

PXRD patterns were collected on a Bruker-AXS Ltd. D4 powder X-ray diffractometer fitted with an automatic sample changer, a theta-theta goniometer, automatic beam divergence slit, and a PSD Vantec-1 detector. The X-ray tube voltage and amperage were set to 35 kV and 40 mA respectively. The diffractometer was aligned and a calibration check performed using a corundum reference material on the day of data collection. Data was collected at the Cu wavelength using a step size of 0.018 degrees and scan time and 11.3 hours scanning from 2.0 to 65.0 degrees 2-theta. The samples were prepared by placing the powder in a slightly greased low background holder. The sample powder was pressed by a glass slide to ensure that a proper sample height was achieved and rotated during collection. Data were collected using Bruker DIFFRAC software and analysis was performed by DIFFRAC EVA software (Version 3.1)

The PXRD patterns collected were imported into Bruker DIFFRAC EVA software. The measured PXRD pattern was aligned with the simulated pattern from single crystal data prior to selecting the peak positions. A peak search was performed using the Bruker software. The peak selection was carefully checked to ensure that all peaks had been captured and all peak positions had been accurately assigned. The peak list for peaks with 2-theta lower than 30 were normalized relative to highest intensity peak equalling 100%. A typical error of ±0.2° 2-theta in peak positions applies to this data. The minor error associated with this measurement can occur as a result of a variety of factors including: (a) sample preparation (e.g., sample height), (b) instrument, (c) calibration, (d) operator (including those errors present when determining the peak locations), and (e) the nature of the material (e.g. preferred orientation and transparency errors). Therefore peaks are considered to have a typical associated error of ±0.2° 2-theta. When two peaks, in the list, are considered to overlap (±0.2° 2-theta) the less intense peak has been removed from the listing. Peaks existing as shoulders, on a higher intensity adjacent peak, have also been removed from the peak list. While the shoulders may be >0.2° 2-theta from the position of the adjacent peak, they are not considered as discernible from the adjacent peak.

Ideally the powder pattern should be aligned against a reference. This could either be the simulated powder pattern from the crystal structure of the same form, or an internal standard e.g. silica. The measured PXRD pattern of Form 1 used to generate the peak listing was aligned to the simulated pattern from single crystal structure.

FT-Raman:

FT-Raman spectra were collected using a RAM II FT Raman module attached to a Vertex 70 FTIR spectrometer. The instrument is equipped with a 1064 nm Nd:YAG laser and a liquid nitrogen cooled germanium detector. Prior to data acquisition, instrument performance and calibration verifications were conducted using a white light source, and polystyrene and naphthalene references.

Samples were analyzed in truncated NMR tubes (5 mm diameter) that were rotated during spectral collection. The backscattered Raman signal from the sample in the rotator was optimized and a spectrum was acquired using the following parameters:

Laser power: 500 mW
Spectral resolution: 2 cm$^{-1}$
Collection range: approximately 4000-50 cm$^{-1}$
Number of scans: 512
Apodization function: Blackmann-Harris 4-term The variability in the peak positions with this experimental configuration is within ±2 cm$^{-1}$.

Prior to peak picking the intensity scale of the Stokes scattered Raman signal was normalized to 1.00 Peaks positions were then identified using the peak picking functionality in the GRAMS/AI v.9.1 software (Thermo Fisher Scientific) with the threshold set to 0.05.

Peaks with relative intensities between 1.00 and 0.75, 0.74 and 0.5, 0.49 and 0.25 and below 0.25 were labelled as very strong, strong, medium and weak respectively.

Solid State $^{13}$C Nuclear Magnetic Resonance Spectroscopy:

Solid state NMR (ssNMR) analysis was conducted on a CPMAS probe positioned into a Bruker-BioSpin Avance III 500 MHz (1H frequency) NMR spectrometer. Material was packed into a 4 mm rotor sealed with a standard drive cap. Data was collected at 5° C. (calibrated by PbNO$_3$). $^{13}$C ssNMR spectra were collected using a proton decoupled cross-polarization magic angle spinning (CPMAS) experiment. A magic angle spinning rate of 15.0 kHz was used. A phase modulated proton decoupling field of 80-90 kHz was applied during spectral acquisition. The cross-polarization contact time was set to 2 ms and the recycle delay to 15 seconds. The number of scans was adjusted to obtain an adequate signal to noise ratio, with 1024 scans being collected for the API and 6144 scans collected for drug products. The carbon chemical shift scale was referenced using a $^{13}$C CPMAS experiment on an external standard of crystalline adamantane, setting its up-field resonance to 29.5 ppm.

Automatic peak picking was performed using Bruker-BioSpin TopSpin version 3.5 software. Generally, a threshold value of 5% relative intensity was used for preliminary peak selection. The output of the automated peak picking was visually checked to ensure validity and adjustments were manually made if necessary. Although specific $^{13}$C solid state NMR peak values are reported herein there does exist a range for these peak values due to differences in instruments, samples, and sample preparation. This is common practice in the art of solid state NMR because of the variation inherent in peak positions. A typical variability for a $^{13}$C chemical shift x-axis value is on the order of plus or minus 0.2 ppm for a crystalline solid. The solid state NMR peak heights reported herein are relative intensities. Solid state NMR intensities can vary depending on the actual setup of the CPMAS experimental parameters and the thermal history of the sample.

The present invention provides a crystalline form of the p-toluenesulfonic acid salt of 1-((2S,5R)-5-((7H-pyrrolo[2,3-d]pyrimidin-4-yl)amino)-2-methyl-piperidin-1-yl)prop-2-en-1-one which can be identified by one or more solid state analytical methods. A PXRD peak list for the crystalline form of the p-toluenesulfonic acid salt of 1-((2S,5R)-5-((7H-pyrrolo[2,3-d]pyrimidin-4-yl)amino)-2-methyl-piperidin-1-yl)prop-2-en-1-one at 23° C. is shown in Table 1. Characteristic peaks are indicated by an asterisk (*).

TABLE 1

| Angle °2-theta | Intensity % |
| --- | --- |
| 10.7 | 12.3 |
| 11.4* | 54.1 |
| 12.8 | 16.5 |
| 14.1* | 13.7 |
| 16.7* | 45.1 |
| 17.9* | 100 |
| 19.5 | 62.0 |
| 20.7 | 22.1 |
| 21.3 | 18.4 |
| 21.6* | 32.8 |
| 21.9 | 27.2 |
| 22.8 | 89.6 |
| 25.3 | 36.3 |

TABLE 1-continued

| Angle °2-theta | Intensity % |
| --- | --- |
| 25.8 | 16.2 |
| 28.1 | 22.7 |

A Raman peak list for the crystalline form, prepared in accordance with the disclosed method is shown in Table 2. Characteristic peaks are indicated by an asterisk (*).

TABLE 2

| Peak Positions/cm$^{-1}$ (±2 cm$^{-1}$) | Relative peak intensity |
| --- | --- |
| 201 * | m |
| 227 | w |
| 294 | m |
| 321 | w |
| 401 | w |
| 547 | w |
| 573 | w |
| 638 * | w |
| 683 | w |
| 737 | w |
| 766 * | m |
| 799 * | m |
| 815 * | w |
| 842 | w |
| 881 | w |
| 906 | w |
| 984 | w |
| 1009 | m |
| 1032 * | m |
| 1040 * | m |
| 1082 | m |
| 1098 | w |
| 1116 | m |
| 1136 | m |
| 1154 | m |
| 1215 | w |
| 1228 | m |
| 1252 | m |
| 1291 | m |
| 1312 | m |
| 1322 | s |
| 1351 | m |
| 1383 | m |
| 1406 | m |
| 1447 | s |
| 1471 | vs |
| 1487 | vs |
| 1574 | w |
| 1601 * | s |
| 1617 * | s |
| 2872 | m |
| 2925 | m |
| 2957 | m |
| 2970 | m |
| 3010 | w |
| 3038 | w |
| 3057 | m |
| 3106 | w |
| 3137 | w |
| 3166 | w |

Solid State $^{13}$C NMR peak list for the crystalline form, prepared in accordance with the disclosed method is shown in Table 3. Characteristic peaks are indicated by an asterisk (*).

TABLE 3

| $^{13}$C Chemical Shifts [ppm] | Intensity |
|---|---|
| 17.3 * | 78 |
| 21.3 * | 82 |
| 26.6 | 54 |
| 28.7 * | 55 |
| 41.6 | 45 |
| 46.5 | 57 |
| 51.0 | 55 |
| 102.3 | 40 |
| 105.6 | 52 |
| 124.3 | 55 |
| 125.3 | 58 |
| 126.1 | 63 |
| 127.5 | 70 |
| 127.9 | 100 |
| 131.6 * | 52 |
| 141.8 | 49 |
| 143.6 | 73 |
| 147.9 * | 28 |
| 149.5 | 29 |
| 165.4 | 33 |

TABLE 4

Examples of key characterization identifiers for the p-toluenesulfonic acid salt of 1-((2S,5R)-5-((7H-pyrrolo[2,3-d]pyrimidin-4-yl)amino)-2-methylpiperidin-1-yl)prop-2-en-1-one (Form 1), using a single or a combination of instrument methods.

| Form 1 | PXRD (2-Theta °) | Raman (cm$^{-1}$) | $^{13}$C ssNMR (ppm) |
|---|---|---|---|
| Single | 11.4, 14.1, 16.7, 17.9 and 21.6 | | |
| Single | | 1617, 1601, 1040, 1032, 799 and 766 | |
| Single | | | 17.3, 21.3, 28.7, 131.6, and 147.9 |
| Combination | 11.4, 16.7, 17.9 | 1617, 1601 | |
| Combination | 11.4, 16.7, 17.9 | | 131.6, 147.9 |
| Combination | | 1617, 1601 | 131.6, 147.9 |
| Combination | 11.4, 16.7, 17.9 | 1617, 1601 | 131.6, 147.9 |
| Combination | 11.4, 14.1, 16.7, 17.9 and 21.6 | 1617, 1601, 1040, 1032, 799 and 766 | 17.3, 21.3, 28.7, 131.6, and 147.9 |

Example 3

Solid State Stability

The solid state stability of the tosylate salt and phosphate salt are significantly improved when compared with both the amorphous free base as well as the malonate salt. The solid state stability is monitored using accelerated stability conditions (70° C./75% RH) for one week and then monitoring appearance, purity and form change. These accelerated conditions are used to assign an initial use period for the API. For the malonate salt, the purity of the API dropped from 99.5% to 81.6% after subjecting it to one week of accelerated conditions. The tosylate salt in comparison was subjected to the accelerated stability conditions and showed a purity decrease from 99.1% to 97.7%. The phosphate salt showed a similarly unexpected improvement in stability over the free base and malonate comparators. Comparative data are set forth in Table 5. Accordingly, the recommended storage condition that was prescribed for the malonate salt of the API would require refrigeration, whereas the tosylate salt would not require refrigerated storage conditions for use as an API.

TABLE 5

| Purity Comparison | Amorphous Free base | Malonate salt | Tosylate salt | Phosphate salt |
|---|---|---|---|---|
| Initial Purity | 99.3% | 99.5% | 99.6% | 99.6% |
| Final Purity (post stress test) | 41.3& | 81.6% | 99.6% | 99.5% |

What is claimed is:

1. A p-toluenesulfonic acid salt of 1-((2S,5R)-5-((7H-pyrrolo[2,3-d]pyrimidin-4-yl)amino)-2-methylpiperidin-1-yl)prop-2-en-1-one, having a powder X-ray diffraction pattern comprising peaks, in terms of 2θ, at 11.4, 14.1, 16.7, 17.9 and 21.6° 2θ±0.2° 2θ.

2. The crystalline form of claim 1, having a powder X-ray diffraction pattern comprising peaks, in terms of 2θ, at 11.4, 16.7, 17.9° 2θ±0.2° 2θ and solid state $^{13}$C nuclear magnetic resonance chemical shifts selected from the group consisting of 131.6, 147.9 ppm±0.2 ppm.

3. The crystalline form of claim 1 having a powder X-ray diffraction pattern comprising peaks, in terms of 2θ, at 11.4, 16.7, 17.9° 2θ±0.2° 2θ and a set of Raman bands at 1617, 1601 cm$^{-1}$±2 cm$^{-1}$.

4. The crystalline form of claim 1 having a powder X-ray diffraction pattern comprising peaks, in terms of 2θ, at 11.4, 16.7, 17.9° 2θ±0.2° 2θ, a set of Raman bands at 1617, 1601 cm$^{-1}$±2 cm$^{-1}$ and solid state $^{13}$C nuclear magnetic resonance chemical shifts selected from the group consisting of 131.6, 147.9 ppm±0.2 ppm.

5. A method of treating psoriasis, comprising administering to a subject suffering from said disease or condition an effective amount of a composition comprising the salt of claim 1.

6. A method of treating vitiligo, comprising administering to a subject suffering from said disease or condition an effective amount of a composition comprising the salt of claim 1.

* * * * *